US011583239B2

(12) United States Patent
Wang et al.

(10) Patent No.: US 11,583,239 B2
(45) Date of Patent: Feb. 21, 2023

(54) METHOD AND SYSTEM OF BUILDING HOSPITAL-SCALE CHEST X-RAY DATABASE FOR ENTITY EXTRACTION AND WEAKLY-SUPERVISED CLASSIFICATION AND LOCALIZATION OF COMMON THORAX DISEASES

(71) Applicant: The United States of America, as represented by the Secretary, Department of Health and Human Services, Bethesda, MD (US)

(72) Inventors: Xiaosong Wang, Rockville, MD (US); Yifan Peng, Bethesda, MD (US); Le Lu, Bethesda, MD (US); Zhiyong Lu, Bethesda, MD (US); Ronald M. Summers, Potomac, MD (US)

(73) Assignee: The United States of America, as represented by the Secretary, Department of Health and Human Service, Bethesda, MD (US)

( * ) Notice: Subject to any disclaimer, the term of this patent is extended or adjusted under 35 U.S.C. 154(b) by 654 days.

(21) Appl. No.: 16/495,012

(22) PCT Filed: Mar. 26, 2018

(86) PCT No.: PCT/US2018/024354
§ 371 (c)(1),
(2) Date: Sep. 17, 2019

(87) PCT Pub. No.: WO2018/176035
PCT Pub. Date: Sep. 27, 2018

(65) Prior Publication Data
US 2020/0093455 A1    Mar. 26, 2020

Related U.S. Application Data

(60) Provisional application No. 62/476,029, filed on Mar. 24, 2017.

(51) Int. Cl.
*G06K 9/00* (2022.01)
*A61B 6/00* (2006.01)
(Continued)

(52) U.S. Cl.
CPC .......... *A61B 6/5217* (2013.01); *G06K 9/6259* (2013.01); *G06N 3/08* (2013.01);
(Continued)

(58) Field of Classification Search
CPC .... G06N 3/084; G06K 9/6256; G06K 9/6261; G06T 3/4038; G06T 5/50; G06T 2207/20021; G06T 2207/20212
See application file for complete search history.

(56) References Cited

U.S. PATENT DOCUMENTS

2011/0035208 A1* 2/2011 Hale ............... G06F 40/242
704/E11.001
2016/0232658 A1* 8/2016 Syeda-Mahmood .........
G06K 9/6267

(Continued)

FOREIGN PATENT DOCUMENTS

CN       106372390       2/2017

OTHER PUBLICATIONS

Binghui Chen, Weihong Deng, "Weakly-supervised deep self-learning for face recognition", 2016 IEEE International Conference on Multimedia and Expo (ICME), Date of Conference: Jul. 11-15, 2016, Date Added to IEEE Xplore: Aug. 29, 2016 (Year: 2016).*

(Continued)

*Primary Examiner* — Atiba O Fitzpatrick
(74) *Attorney, Agent, or Firm* — Polsinelli PC

(57) ABSTRACT

A new chest X-ray database, referred to as "ChestX-ray8", is disclosed herein, which comprises over 100,000 frontal view X-ray images of over 32,000 unique patients with the text-mined eight disease image labels (where each image (Continued)

| Radiology report | Keyword | Localization Result |
|---|---|---|
| findings: pa and lateral views of the chest demonstrate stable 2.2 cm nodule in left lower lung field posteriorly. the lungs are clear without infiltrate or effusion. cardiomediastinal silhouette is normal size and contour. pulmonary vascularity is normal in caliber and distribution. impression: stable left likely hamartoma. | Nodule; Infiltration |  | can have multi-labels), from the associated radiological reports using natural language processing. We demonstrate that these commonly occurring thoracic diseases can be detected and spatially-located via a unified weakly supervised multi-label image classification and disease localization framework, which is validated using our disclosed dataset.

18 Claims, 12 Drawing Sheets

(51) Int. Cl.
| | |
|---|---|
| G16H 30/20 | (2018.01) |
| G16H 50/70 | (2018.01) |
| G16H 50/20 | (2018.01) |
| G06K 9/62 | (2022.01) |
| G06N 3/08 | (2023.01) |
| G06T 7/00 | (2017.01) |

(52) U.S. Cl.
CPC .......... *G06T 7/0014* (2013.01); *G16H 30/20* (2018.01); *G16H 50/20* (2018.01); *G16H 50/70* (2018.01); *G06T 2207/10116* (2013.01); *G06T 2207/20081* (2013.01); *G06T 2207/20084* (2013.01); *G06T 2207/30061* (2013.01); *G06T 2210/12* (2013.01)

(56) References Cited

U.S. PATENT DOCUMENTS

2017/0372007 A1* 12/2017 Lu ...................... G06F 16/5866
2018/0144209 A1    5/2018 Kim et al.

OTHER PUBLICATIONS

International Search Report and Written Opinion for related International Application No. PCT/US2018/024354, dated Jul. 19, 2018, 12 pages.
Shin et al., "Interleaved Text/Image Deep Mining on a Large-Scale Radiology Database for Automated Image Interpretation," *Journal of Machine Learning Research*, 17:1-31 (Jun. 1, 2016).
Shin et al., "Learning to Read Chest X-Rays: Recurrent Neural Cascade Model for Automated Image Annotation," *IEEE Conference on Computer Vision and Pattern Recognition (CVPR)*, pp. 2497-2506, Las Vegas, NV (Jun. 27-30, 2016).
Suzuki, "Pixel-Based Machine Learning in Medical Imaging," *International Journal of Biomedical Imaging*, 2012(792079):1-18 (Feb. 28, 2012).
Wang et al., "ChestX-ray8: Hospital-scale Chest X-ray Database and Benchmarks on Weakly-Supervised Classification and Localization of Common thorax Diseases," *IEEE Conference on computer Vision and Pattern Recognition (CVPR)*, Honolulu, HI, pp. 2097-2106 (Jul. 21-26, 2017).
Xue et al., "Chest X-ray Image View Classification," *IEEE Symposium on Computer-Based Medical Systems*, 6 pages (Jul. 1, 2015).
Zakirov et al., "Advanced Approaches to Computer-Aided Detection of Thoracic Diseases on Chest X-Rays," 9(88):4361-4369 (Jan. 1, 2015).
Open-i: An open access biomedical search engine. https://openi.nlm.nih.gov. 3, 1 page, obtained Jan. 14, 2020.
Agrawal, et al., "VQA: Visual Question Answering," arXiv:1505.00468v6, 23 pages (Apr. 20, 2016).
Aronson, et al., "An overview of MetaMap: historical perspective and recent advances," *Journal of the American Medical Informatics Association*, 17(3):229-236 (May 4, 2010).
Ba, et al., "Predicting Deep Zero-Shot Convolutional Neural Networks Using Textual Descriptions," *Computer Vision Foundation*, pp. 4247-4255 (Jun. 1, 2015).

Bird, et al., "Natural language processing with Python," O'Reilly Media, Inc., chapters, 1, 3, and 6, 131 pages (Jun. 2009).
Chapman, et al., "A Simple Algorithm for Identifying Negated Findings and Diseases in Discharge Summaries," *Journal of Biomedical Informatics*, 34(5):301-310 (Oct. 2001).
Charniak, et al., "Coarse-to-fine n-best parsing and MaxEnt discriminative reranking," In Proceedings of the 43rd Annual Meeting on Association for Computational Linguistics (ACL), pp. 173-180 (Jun. 2005).
De Marneffe et al., "Stanford typed dependencies manual." Stanford University, 28 pages (Sep. 2008).
Demner-Fushman,et al., "Preparing a collection of radiology examinations for distribution and retrieval," *Journal of the American Medical Informatics Association*, 23(2):304-310 (Jul. 1, 2015).
Deng, et al., "ImageNet: A large-scale hierarchical image database.," *Computer Vision and Pattern Recognition*, pp. 248-255, (Jun. 20-25, 2009).
Dou, et al., "Automatic Detection of Cerebral Microbleeds from MR Images Via 3D Convolutional Neural Networks," *IEEE Transactions on Medical Imaging*, 35(5):1182-1195 (Feb. 2016).
Durand, et al., "WELDON: Weakly Supervised Learning of Deep Convolutional Neural Networks," *IEEE CVPR*, 10 pages (Jun. 30, 2016).
Everingham, et al., "The PASCAL Visual Object Classes Challenge: A Retrospective," *International Journal of Computer Vision*, 111(1):98-136 (Jan. 2015).
Greenspan, et al., "Guest Editorial Deep Learning in Medical Imaging: Overview and Future Promise of an Exciting New Technique," *IEEE Transactions on Medical Imaging*, 35(5):1153-1159 (May 2016).
Hariharan et al., "Low-shot visual object recognition," arXiv:1606.02819v1, 10 pages, (Jun. 9, 2016).
Havaei, et al., "HeMIS: Hetero-Modal Image Segmentation," arXiv:1607.05194v1, 11 pages, (Jul. 18, 2016).
He, et al., "Deep Residual Learning for Image Recognition," IEEE Conference on Computer Vision Foundation, pp. 770-778 (Jun. 27-30, 2016).
Hosang et al., "What makes for effective detection proposals?" *IEEE Transactions on Pattern Analysis and Machine Intelligence*, 38(4):814-830 (Apr. 1, 2016).
Hwang et al., "Self-transfer learning for weakly supervised lesion localization," arXiv:1602.01625v1, 9 pages (Feb. 4, 2016).
Jaeger, et al., "Two public chest x-ray datasets for computer-aided screening of pulmonary diseases," *Quantitative Imaging in Medicine and Surgery*, 4(6):475-477 (Nov. 15, 2014).
Jamaludin, et al., "SpineNet: Automatically Pinpointing Classification Evidence in Spinal MRIs," *Medical Image Computing and Computer-Assisted Intervention*, pp. 166-175 (Oct. 2, 2016).
Jia, et al., "Caffe: Convolutional Architecture for Fast Feature Embedding," arXiv:1408.5093v1, 4 pages (Jun. 20, 2014).
Johnson, et al., "DenseCap: Fully Convolutional Localization Networks for Dense Captioning," In *CVPR*, pp. 4565-4574 (Nov. 2015).
Karpathy, et al., "Deep visual-semantic alignments for generating image descriptions," In *IEEE*, 39(4):664-676 (Apr. 1, 2017).
Krishna, et al., "Visual Genome: Connecting Language and Vision Using Crowdsourced Dense Image Annotations," arXiv:1602.07332v1, 44 pages (Feb. 2016).
Krizhevsky, et al., "ImageNet Classification with Deep Convolutional Neural Networks," In *Advances in Neural Information Processing Systems*, 9 pages (2012).
Leaman, et al., "Challenges in clinical natural language processing for automated disorder normalization," *Journal of Biomedical Informatics*, 57:28-37 (Jul. 14, 2015).
Lin, et al., "Microsoft COCO: Common Objects in Context," arXiv:1405.0312v3, 15 pages (Feb. 21, 2015).
McClosky. "Any domain parsing: automatic domain adaptation for natural language parsing," Thesis, Department of Computer Science, Brown University 2 pages, (Sep. 18, 2009).
Moeskops, et al., "Deep Learning for Multi-Task Medical Image Segmentation in Multiple Modalities," arXiv:1704.03379v1, 9 pages (Apr. 11, 2017).

(56) References Cited

OTHER PUBLICATIONS

Oquab, et al., "Is object localization for free?—Weakly-supervised learning with convolutional neural networks," In *IEEE CVPR*, pp. 685-694 (Jun. 12, 2015).

Pinheiro, et al., "From Image-Level to Pixel-level Labeling with Convolutional Networks," In *Proceedings of the IEEE Conference on Computer Vision and Pattern Recognition*, pp. 1713-1721 (Jun. 12, 2015).

Plummer, et al., "Flickr30k entities: Collecting region to-phrase correspondences for richer image-to-sentence models," In *ICCV*, pp. 2641-2649 (May 2015).

Qiao, et al., "Less is more: zero-shot learning from online textual documents with noise suppression," In *CVPR*, pp. 2249-2257 (Apr. 2016).

Ronneberger, et al., "U-Net: Convolutional Networks for Biomedical Image Segmentation," arXiv:1505.04597v1, 8 pages (May 18, 2015).

Roth, et al., Deeporgan: Multi-level deep convolutional networks for automated pancreas segmentation. In *MICCAI*, pp. 556-564. Springer (Jun. 2015).

Roth, et al., "A New 2.5D Representation for Lymph Node Detection using Random Sets of Deep Convolutional Neural Network Observations," arXiv:1406.2639v1, 12 pages (Jun. 6, 2014).

Russakovsky, et al. "ImageNet Large Scale Visual Recognition Challenge," *International Journal of Computer Vision*, 115(3):211-252 (Jan. 30, 2015).

Setio, et al., "Pulmonary Nodule Detection in CT Images: False Positive Reduction Using Multi-View Convolutional Networks," *IEEE Transactions on Medical Imaging*, 35(5):1160-1169 (May 2016).

Shin, et al., "Deep convolutional neural networks for computer-aided detection: Cnn architectures, dataset characteristics and transfer learnings." *IEEE Trans. Medical Imaging*, 35(5):1285-1298 (May 2016).

Simonyan, et al., "Very Deep Convolutional Networks for Large-Scale Image Recognition," arXiv:1409.1556v6, 14 page, Apr. 10, 2015.

Szegedy, et al., "Going deeper with convolutions," arXiv:1409.4842v1, 12 pages (Sep. 17, 2014).

Tapaswi, et al., "MovieQA: Understanding Stories in Movies Through Question-Answering." *Computer Vision Foundation*, pp. 4631-4640 (Dec. 9, 2015).

Uijlings, et al., "Selective search for object recognition." *International Journal of Computer Vision*, 104(2):154-171 (Sep. 2013.

Vendrov, et al. "Order-Embeddings of Images and Language." *ICLR*, 13 pages (May 27, 2016).

Vinyals, et al., "Show and tell: A neural image caption generator." *IEEE Conference on Computer vision and Pattern Recognition*, pp. 3156-3164 (Jun. 2015).

Wilke, et al., "The benefits of multi-disciplinary research on intervertebral disc degeneration." *European Spine Journal*, 23(3):303-304 (Jun. 2016).

Wu, et al., "Ask me anything: free-form visual question answering based on knowledge from external sources." *Computer Vision Foundation*, pp. 4622-4630 (Apr. 14, 2016).

Yao et al., "A multi-center milestone study of clinical vertebral CT segmentation." *Computerized Medical Imaging and Graphics*, 49:16-28 (Apr. 2016).

Young, et al., "From image descriptions to visual denotations: New similarity metrics for semantic inference over event descriptions." *Transactions of the Association for Computational Linguistics*, 2:67-78 (Dec. 1, 2014).

Zhou, et al., "Learning deep features for discriminative localization." *Computer Vision Foundation*, pp. 2921-2929 (Dec. 14, 2015).

Zhu, et al., "Visual7w: Grounded question answering in images." *Computer Vision Foundation*, pp. 4995-5004 (Apr. 9, 2016).

\* cited by examiner

| Radiology report | Keyword | Localization Result |
|---|---|---|
| findings include: 1. left basilar atelectasis/consolidation. 2. prominent hilum (mediastinal adenopathy). 3. left pic catheter (tip in atriocaval junction). 4. stable, normal appearing cardiomediastinal silhouette. impression: small right pleural effusion otherwise stable abnormal study including left basilar infiltrate/atelectasis, prominent hilum, and position of left pic catheter (tip atriocaval junction). | Effusion; Infiltration; Atelectasis | 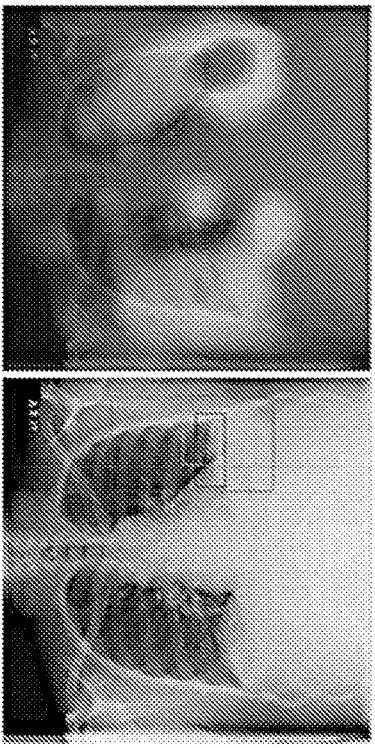 |

FIG. 7

| Radiology report | Keyword | Localization Result |
|---|---|---|
| findings include: 1. cardiomegaly (ct ratio of 17/30). 2. otherwise normal lungs and mediastinal contours. 3. no evidence of focal bone lesion. dictating | Cardiomegaly | 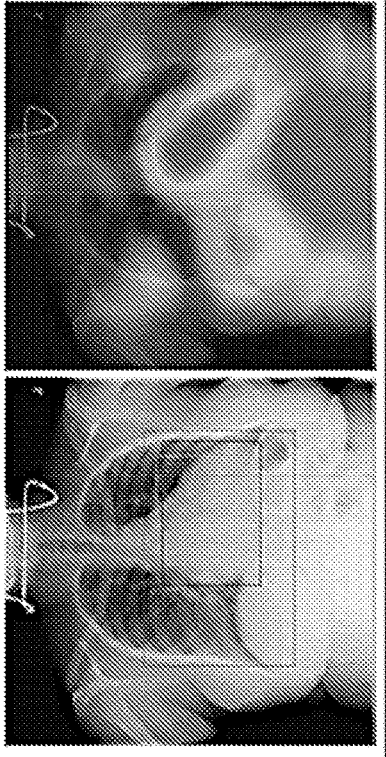 |

FIG. 8

METHOD AND SYSTEM OF BUILDING HOSPITAL-SCALE CHEST X-RAY DATABASE FOR ENTITY EXTRACTION AND WEAKLY-SUPERVISED CLASSIFICATION AND LOCALIZATION OF COMMON THORAX DISEASES

CROSS REFERENCE TO RELATED APPLICATIONS

This is the U.S. National Stage of International Application No. PCT/US2018/024354, filed Mar. 26, 2019, which was published in English under PCT Article 21(2), which in turn claims the benefit of U.S. Provisional Application No. 62/476,029, filed Mar. 24, 2017, which is incorporated by reference herein in its entirety.

STATEMENT OF GOVERNMENT SUPPORT

This invention was made with Government support by the National Institutes of Health, National Cancer Institute, Clinical Center. The United States Government has certain rights in the invention.

FIELD

This application related to classifying and localizing thorax diseases using medical imaging and machine intelligence.

BACKGROUND

The chest X-ray is one of the most commonly accessible radiological examinations for screening and diagnosis of many lung diseases. A tremendous number of X-ray imaging studies accompanied by radiological reports are accumulated and stored in many modern hospitals' Picture Archiving and Communication Systems (PACS). On the other side, it is still an open question how this type of hospital-size knowledge database containing invaluable imaging informatics (i.e., loosely labeled) can be used to facilitate the data-hungry deep learning paradigms in building truly large-scale high precision computer-aided diagnosis (CAD) systems.

SUMMARY

Disclosed herein is new chest X-ray database, referred to as "ChestX-ray8", which comprises 108,948 frontal view X-ray images of 32,717 unique patients with the text mined eight disease image labels (where each image can have multi-labels), from the associated radiological reports using natural language processing. We demonstrate that these commonly occurring thoracic diseases can be detected and spatially-located via a unified weakly supervised multi-label image classification and disease localization framework, which is validated using our disclosed dataset. The initial quantitative results are described herein, and furthermore deep convolutional neural network based "reading chest X-rays" (e.g., recognizing and locating the common disease patterns trained with only image-level labels) can also be performed with fully-automated high precision CAD systems.

The foregoing and other features and advantages of the disclosed technology will become more apparent from the following detailed description, which proceeds with reference to the accompanying figures.

BRIEF DESCRIPTION OF THE FIGURES

FIG. 7 is a sample of a chest x-ray radiology report, with mined disease keywords and localization result from the "Atelectasis" Class. Correct bounding box (in green), false positives (in red) and the ground truth (in blue) are plotted over the original image.

FIG. 8 is a sample of a chest x-ray radiology report, with mined disease keywords and localization result from the "Cardiomegaly" Class. Correct bounding box (in green), false positives (in red) and the ground truth (in blue) are plotted over the original image.

DETAILED DESCRIPTION

Figure 1:
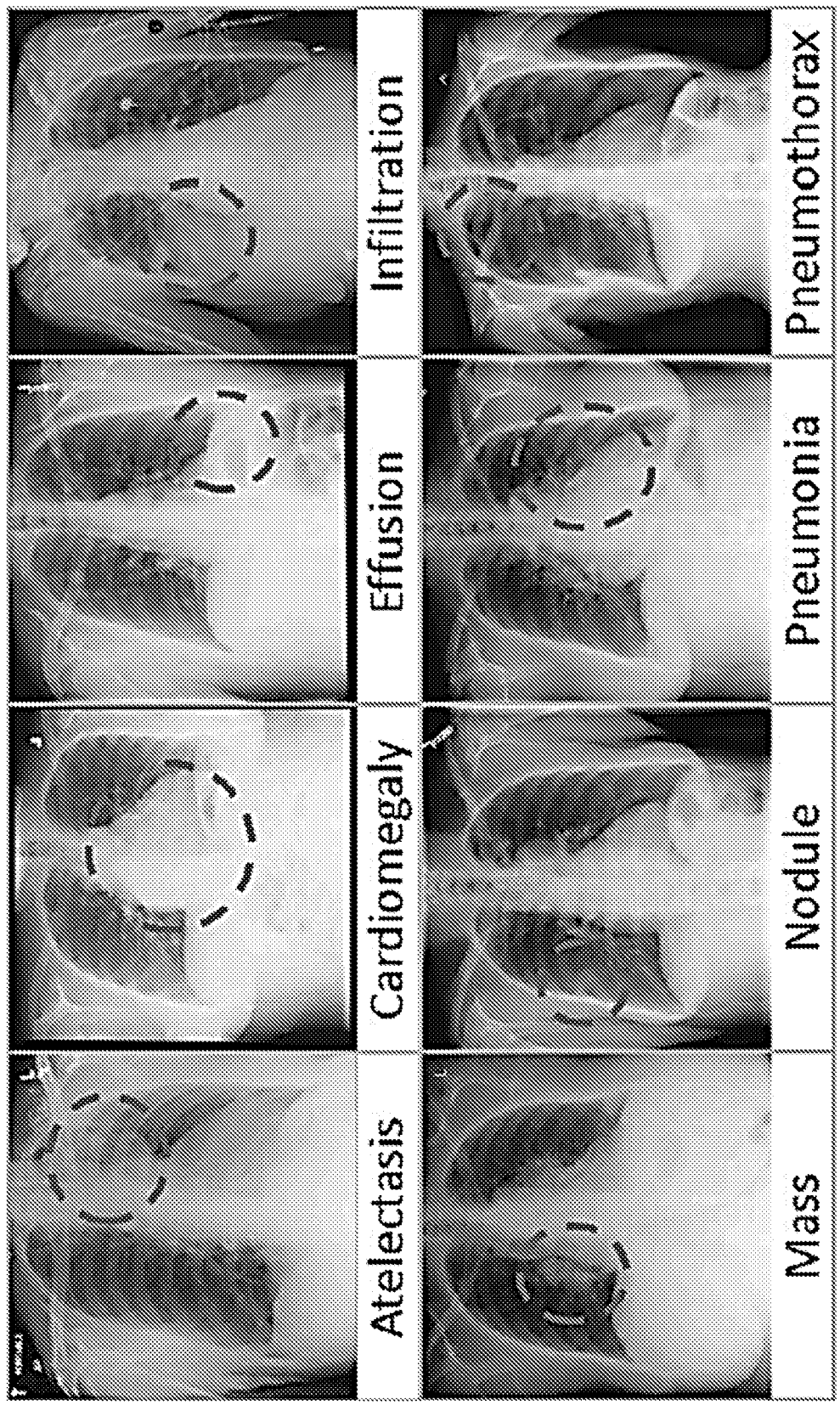
FIG. 1 illustrates eight common thoracic diseases observed in chest X-rays that validate a challenging task of fully-automated diagnosis.

As described herein, rapid and tremendous progress has been evidenced in a range of computer vision problems via deep learning and large-scale annotated image datasets. Drastically improved quantitative performances in object recognition, detection, and segmentation are demonstrated in comparison to previous shallow methodologies built upon hand-crafted image features. Deep neural network representations further make the joint language and vision learning tasks more feasible to solve, in image captioning, visual question answering and knowledge-guided transfer learning, and so on. However, the intriguing and strongly observable performance gaps of the current state-of-the-art object detection and segmentation methods, evaluated between using PASCAL VOC and employing Microsoft (MS) COCO, demonstrate that there is still significant room for performance improvement when underlying challenges (represented by different datasets) become greater. For example, MS COCO is composed of 80 object categories from 200k images, with 1.2M instances (350k are people) where every instance is segmented and many instances are small objects. Comparing to PASCAL VOC of only 20 classes and 11,530 images containing 27,450 annotated objects with bounding-boxes (BBox), an alternative object detection approaches achieve 0.413 in MS COCO versus 0.884 in PASCAL VOC, under mean Average Precision (mAP).

Deep learning yields similar rises in performance in the medical image analysis domain for object (often human anatomical or pathological structures in radiology imaging) detection and segmentation tasks. Recent notable work includes (but is not limit to) an overview review on the future promise of deep learning and a collection of important medical applications on lymph node and interstitial lung disease detection and classification; cerebral microbleed detection; pulmonary nodule detection in CT images; automated pancreas segmentation; cell image segmentation and tracking, predicting spinal radiological scores, and extensions of multi-modal imaging segmentation. A significant limitation is that all proposed methods are evaluated on some small-to-middle scale problems of (at most) several hundred patients. It remains unclear how well the current deep learning techniques can scale up to tens of thousands of patient studies.

In the era of deep learning in computer vision, research efforts on building various annotated image datasets with different characteristics play important roles on the better definition of the forthcoming problems, challenges and subsequently possible technological progresses. Particularly, here we focus on the relationship and joint learning of image (chest X-rays) and text (X-ray reports). The previous representative image caption generation work utilize Flickr8K, Flickr30K and MS COCO datasets that hold 8,000, 31,000 and 123,000 images respectively and every image is annotated by five sentences via Amazon Mechanical Turk (AMT). The text generally describes annotator's attention of objects and activity occurring on an image in a straightforward manner Region-level ImageNet pre-trained convolutional neural networks (CNN) based detectors are used to parse an input image and output a list of attributes or "visually-grounded high-level concepts" (including objects, actions, scenes and so on) in. Visual question answering (VQA) requires more detailed parsing and complex reasoning on the image contents to answer the paired natural language questions. A new dataset containing 250k natural images, 760k questions and 10M text answers is provided to address this new challenge. Additionally, databases such as "Flickr30k Entities", "Visual7W" and "Visual Genome" (as detailed as 94,000 images and 4,100,000 region-grounded captions) are introduced to construct and learn the spatially-dense and increasingly difficult semantic links between textual descriptions and image regions through the object-level grounding.

Though one could argue that the high-level analogy exists between image caption generation, visual question answering, and imaging based disease diagnosis, there are at least three factors making truly large-scale medical image based diagnosis (e.g., involving tens of thousands of patients) tremendously more formidable. 1, Generic, open-ended image-level anatomy and pathology labels cannot be obtained through crowd-sourcing, such as AMT, which is prohibitively implausible for non-medically trained annotators. Therefore we exploit to mine the per-image (possibly multiple) common thoracic pathology labels from the image-attached chest X-ray radiological reports using Natural Language Processing (NLP) techniques. Radiologists tend to write more abstract and complex logical reasoning sentences than the plain describing texts in. 2, The spatial dimensions of a chest X-ray are usually 2000×3000 pixels. Local pathological image regions can show hugely varying sizes or extents but often very small comparing to the full image scale. FIG. 1 shows eight illustrative examples and the actual pathological findings are often significantly smaller (thus harder to detect). Fully dense annotation of region-level bounding boxes (for grounding the pathological findings) would normally be needed in computer vision datasets but may be completely nonviable for the time being. Consequently, we formulate and verify a weakly-supervised multi-label image classification and disease localization framework to address this difficulty. 3, So far, all image captioning and VQA techniques in computer vision strongly depend on the ImageNet pre-trained deep CNN models which already perform very well in a large number of object classes and serves a good baseline for further model fine-tuning. However, this situation does not apply to the medical image diagnosis domain. Thus we have to learn the deep image recognition and localization models while constructing the weakly-labeled medical image database.

To tackle these issues, we propose a new chest X-ray database, namely "ChestX-ray8", which comprises 108,948 frontal-view X-ray images of 32,717 (collected from the year of 1992 to 2015) unique patients with the text-mined eight common disease labels, mined from the text radiological reports via NLP techniques. In particular, we demonstrate that these commonly occurred thoracic diseases can be detected and even spatially-located via a unified weakly-supervised multi-label image classification and disease localization formulation.

There have been recent efforts on creating openly available annotated medical image databases with the studied patient numbers ranging from a few hundreds to two thousands. Particularly for chest X-rays, the largest public dataset is OpenI that contains 3,955 radiology reports from the Indiana Network for Patient Care and 7,470 associated chest x-rays from the hospitals picture archiving and communication system (PACS). This database is utilized in as a problem of caption generation but no quantitative disease detection results are reported. Our newly proposed chest X-ray database is at least one order of magnitude larger than OpenI (Refer to Table 1). To achieve the better clinical relevance, we focus to exploit the quantitative performance on weakly-supervised multi-label image classification and disease localization of common thoracic diseases, in analogy to the intermediate step of "detecting attributes" in or "visual grounding" for.

Figure 2:
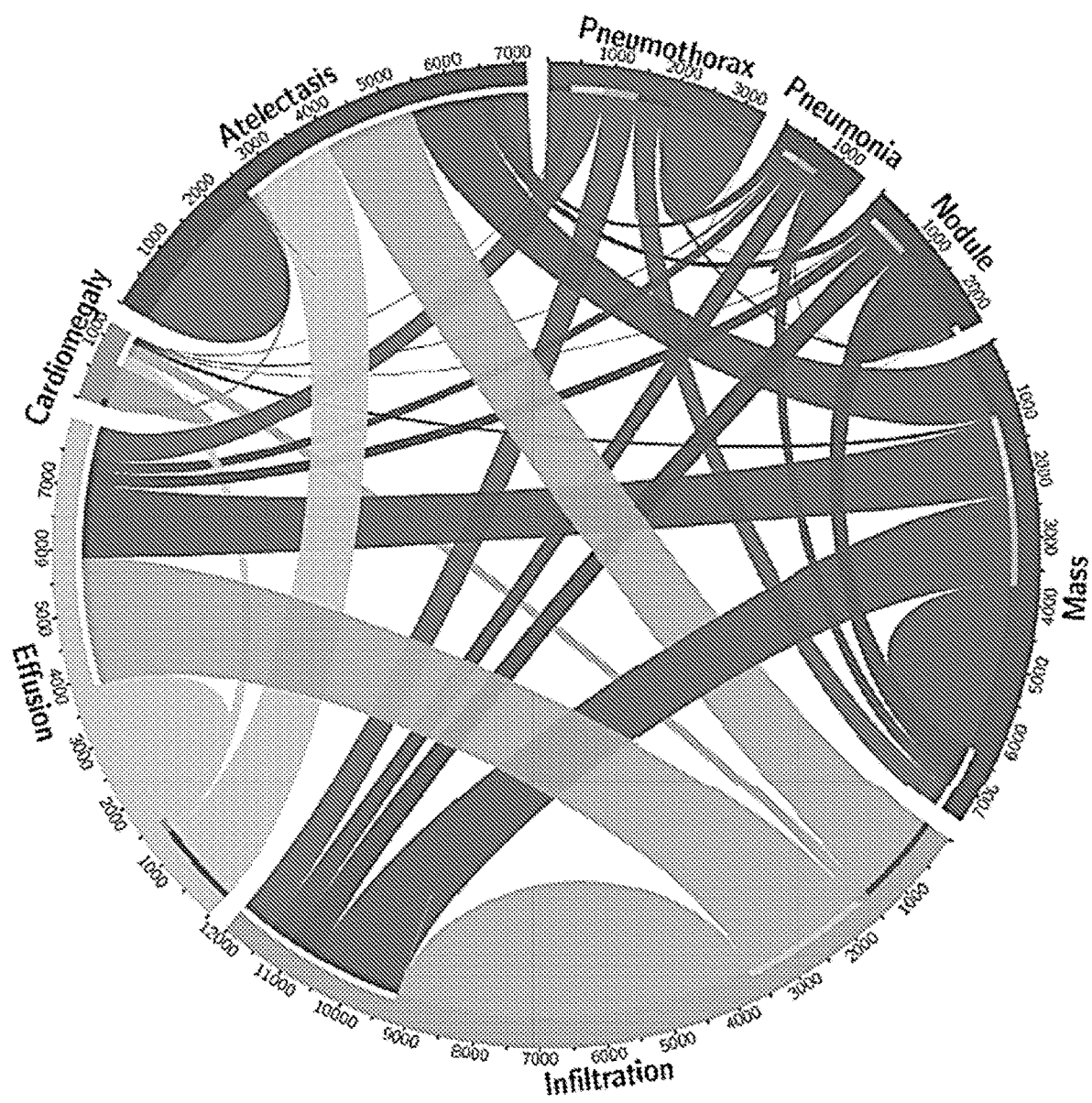
FIG. 2 is a circular diagram that shows the proportions of images with multi-labels in each of eight pathology classes and the labels' co-occurrence statistics.

In this section, we describe the approach for building a hospital-scale chest X-ray image database, namely "ChestX-ray8", mined from our institute's PACS system. First, we short-list eight common thoracic pathology keywords that are frequently observed and diagnosed, i.e., Atelectasis, Cardiomegaly, Effusion, Infiltration, Mass, Nodule, Pneumonia and Pneumathorax (FIG. 1), based on radiologists' feedback. Given those 8 text keywords, we search the PACS system to pull out all the related radiological reports (together with images) as our target corpus. A variety of Natural Language Processing (NLP) techniques are adopted for detecting the pathology keywords and removal of negation and uncertainty. Each radiological report will be either linked with one or more keywords or marked with 'Normal' as the background category. As a result, the ChestX-ray8 database is composed of 108,948 frontal-view X-ray images (from 32,717 patients) and each image is labeled with one or multiple pathology keywords or "Normal" otherwise. FIG. 2 illustrates the correlation of the resulted keywords. It reveals some connections between different pathologies, which agree with radiologists' domain knowledge, e.g., Infiltration is often associated with Atelectasis and Effusion. To some extent, this is similar with understanding the interactions and relationships among objects or concepts in natural images.

Overall, our approach produces labels using the reports in two passes. In the first iteration, we detected all the disease concept in the corpus. The main body of each chest X-ray report is generally structured as "Comparison", "Indication", "Findings", and "Impression" sections. Here, we focus on detecting disease concepts in the Findings and Impression sections. If a report contains neither of these two sections, the full-length report will then be considered. In the second pass, we code the reports as "Normal" if they do not contain any diseases (not limited to 8 predefined pathologies).

Pathology Detection: We mine the radiology reports for disease concepts using two tools, DNorm and MetaMap. DNorm is a machine learning method for disease recognition and normalization. It maps every mention of keywords in a report to a unique concept ID in the Systematized Nomenclature of Medicine Clinical Terms (or SNOMED-CT), which is a standardized vocabulary of clinical terminology for the electronic exchange of clinical health information.

MetaMap is another prominent tool to detect bio-concepts from the biomedical text corpus. Different from DNorm, it is an ontology-based approach for the detection of Unified Medical Language System (UMLS) Metathesaurus. In this work, we only consider the semantic types of Diseases or Syndromes and Findings (namely 'dsyn' and 'fndg' respectively). To maximize the recall of our automatic disease detection, we merge the results of DNorm and MetaMap. Table 5 shows the corresponding SNOMED-CT concepts that are relevant to the eight target diseases (these mappings are developed by searching the disease names in the UMLS terminology service, and verified by a board certified radiologist).

Negation and Uncertainty: The disease detection algorithm locates every keyword mentioned in the radiology report no matter if it is truly present or negated. To eliminate the noisy labeling, we need to rule out those negated pathological statements and, more importantly, uncertain mentions of findings and diseases, e.g., "suggesting obstructive lung disease".

Although many text processing systems can handle the negation/uncertainty detection problem, most of them exploit regular expressions on the text directly. One of the disadvantages to use regular expressions for negation/uncertainty detection is that they cannot capture various syntactic constructions for multiple subjects. For example, in the phrase of "clear of A and B", the regular expression can capture "A" as a negation but not "B", particularly when both "A" and "B" are long and complex noun phrases ("clear of focal airspace disease, pneumothorax, or pleural effusion" in FIG. 3).

To overcome this complication, we hand-craft a number of novel rules of negation/uncertainty defined on the syntactic level in this work. More specifically, we utilize the syntactic dependency information because it is close to the semantic relationship between words and thus has become prevalent in biomedical text processing. We defined our rules on the dependency graph, by utilizing the dependency label and direction information between words.

Figure 3:
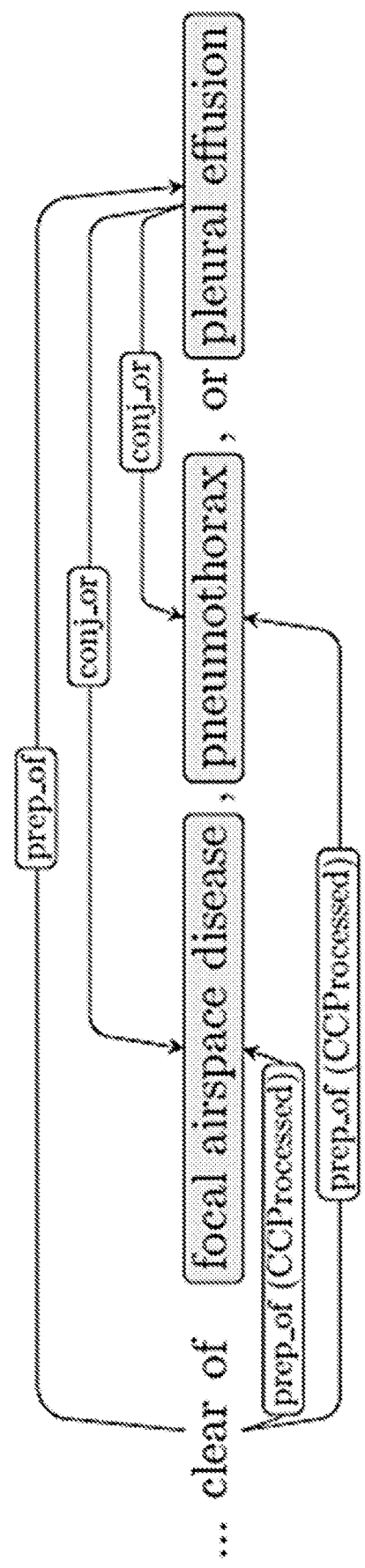
FIG. 3 is a dependency graph of text: "clear of focal airspace disease, pneumothorax, or pleural effusion".

As the first step of preprocessing, we split and tokenize the reports into sentences using NLTK. Next we parse each sentence by the Bllip parser using David McClosky's biomedical model. The syntactic dependencies are then obtained from "CCProcessed" dependencies output by applying Stanford dependencies converter on the parse tree. The "CCProcessed" representation propagates conjunct dependencies thus simplifies coordinations. As a result, we can use fewer rules to match more complex constructions. For an example as shown in FIG. 3, we could use "clear-→prep_of→DISEASE" to detect three negations from the text (neg, focal airspace disease), (neg, pneumothorax), and (neg, pleural effusion).

Furthermore, we label a radiology report as "normal" if it meets one of the following criteria:
  If there is no disease detected in the report. Note that here we not only consider 8 diseases of interest in this paper, but all diseases detected in the reports.
  If the report contains text-mined concepts of "normal" or "normal size" (CUIs C0205307 and C0332506 in the SNOMED-CT concepts respectively).

To validate our method, we perform the following experiments. Given the fact that no gold-standard labels exist for our dataset, we resort to some existing annotated corpora as an alternative. Using the OpenI API, we retrieve a total of 3,851 unique radiology reports where each OpenI report is assigned with its key findings/disease names by human annotators. Given our focus on the eight diseases, a subset of OpenI reports and their human annotations are used as the gold standard for evaluating our method. Table 1 summarizes the statistics of the subset of OpenI reports. Table 2 shows the results of our method using OpenI, measured in precision (P), recall (R), and F1-score. Higher precision of 0.90, higher recall of 0.91, and higher F1-score of 0.90 are achieved compared to the existing MetaMap approach (with NegEx enabled). For all diseases, our method obtains higher precisions, particularly in "pneumothorax" (0.90 vs. 0.32) and "infiltration" (0.74 vs. 0.25). This indicates that the usage of negation and uncertainty detection on syntactic level successfully removes false positive cases. More importantly, the higher precisions meet our expectation to generate a Chest X-ray corpus with accurate semantic labels, to lay a solid foundation for the later processes.

TABLE 1

Total number (#) and # of Overlap (Ov.) of the corpus in both OpenI and ChestX-ray8 datasets.

| Item # | OpenI | Ov. | ChestX-ray8 | Ov. |
|---|---|---|---|---|
| Report | 2,435 | — | 108,948 | — |
| Annotations | 2,435 | — | — | — |
| Atelectasis | 315 | 122 | 5,789 | 3,286 |
| Cardiomegaly | 345 | 100 | 1,010 | 475 |

TABLE 1-continued

Total number (#) and # of Overlap (Ov.) of the
corpus in both OpenI and ChestX-ray8 datasets.

| Item # | OpenI | Ov. | ChestX-ray8 | Ov. |
|---|---|---|---|---|
| Effusion | 153 | 94 | 6,331 | 4,017 |
| Infiltration | 60 | 45 | 10,317 | 4,698 |
| Mass | 15 | 4 | 6,046 | 3,432 |
| Nodule | 106 | 18 | 1,971 | 1,041 |
| Pneumonia | 40 | 15 | 1,062 | 703 |
| Pneumothorax | 22 | 11 | 2,793 | 1,403 |
| Normal | 1,379 | 0 | 84,312 | 0 |

TABLE 2

Evaluation of image labeling results on OpenI dataset.
Performance is reported using P, R, F1-score.

| Disease | MetaMap P/R/F | Our Method P/R/F |
|---|---|---|
| Atelectasis | 0.95/0.95/0.95 | 0.99/0.85/0.91 |
| Cardiomegaly | 0.99/0.83/0.90 | 1.00/0.79/0.88 |
| Effusion | 0.74/0.90/0.81 | 0.93/0.82/0.87 |
| Infiltration | 0.25/0.98/0.39 | 0.74/0.87/0.80 |
| Mass | 0.59/0.67/0.62 | 0.75/0.40/0.52 |
| Nodule | 0.95/0.65/0.77 | 0.96/0.62/0.75 |
| Normal | 0.93/0.90/0.91 | 0.87/0.99/0.93 |
| Pneumonia | 0.58/0.93/0.71 | 0.66/0.93/0.77 |
| Pneumothorax | 0.32/0.82/0.46 | 0.90/0.82/0.86 |
| Total | 0.84/0.88/0.86 | 0.90/0.91/0.90 |

Comparing to the popular ImageNet classification problem, significantly smaller spatial extents of many diseases inside the typical X-ray image dimensions of 3000×2000 pixels impose challenges in both the capacity of computing hardware and the design of deep learning paradigm. In ChestX-ray8, X-rays images are directly extracted from the DICOM file and resized as 1024×1024 bitmap images without significantly losing the detail contents, compared with image sizes of 512×512 in OpenI dataset. Their intensity ranges are rescaled using the default window settings stored in the DICOM header files.

As part of the ChestX-ray8 database, a small number of images with pathology are provided with hand labeled bounding boxes (B-Boxes), which can be used as the ground truth to evaluate the disease localization performance. Furthermore, it could also be adopted for one/low-shot learning setup, in which only one or several samples are needed to initialize the learning and the system will then evolve by itself with more unlabeled data. We leave this as future work. In our labeling process, we first select 200 instances for each pathology (1,600 instances total), consisting of 983 images. Given an image and a disease keyword, a board certified radiologist identified only the corresponding disease instance in the image and labeled it with a B-Box. The B-Box is then outputted as an XML file. If one image contains multiple disease instances, each disease instance is labeled separately and stored into individual XML files. As an application of the proposed ChestX-ray8 database and benchmarking, we will demonstrate the detection and localization of thoracic diseases in the following.

Reading and diagnosing Chest X-ray images may seem to be simple task for radiologists but, in fact, it is a complex reasoning problem which often requires careful observation and good knowledge of anatomical principles, physiology and pathology. Such factors increase the difficulty of developing a consistent and automated technique for reading chest X-ray images while simultaneously considering all common thoracic diseases.

As an important application of ChestX-ray8 dataset, we present a unified weakly-supervised multi-label image classification and pathology localization framework, which can detect the presence of multiple pathologies and subsequently generate bounding boxes around the corresponding pathologies. In details, we tailor Deep Convolutional Neural Network (DCNN) architectures for weakly-supervised object localization, by considering large image capacity, various multi-label CNN losses and different pooling strategies.

Figure 4:
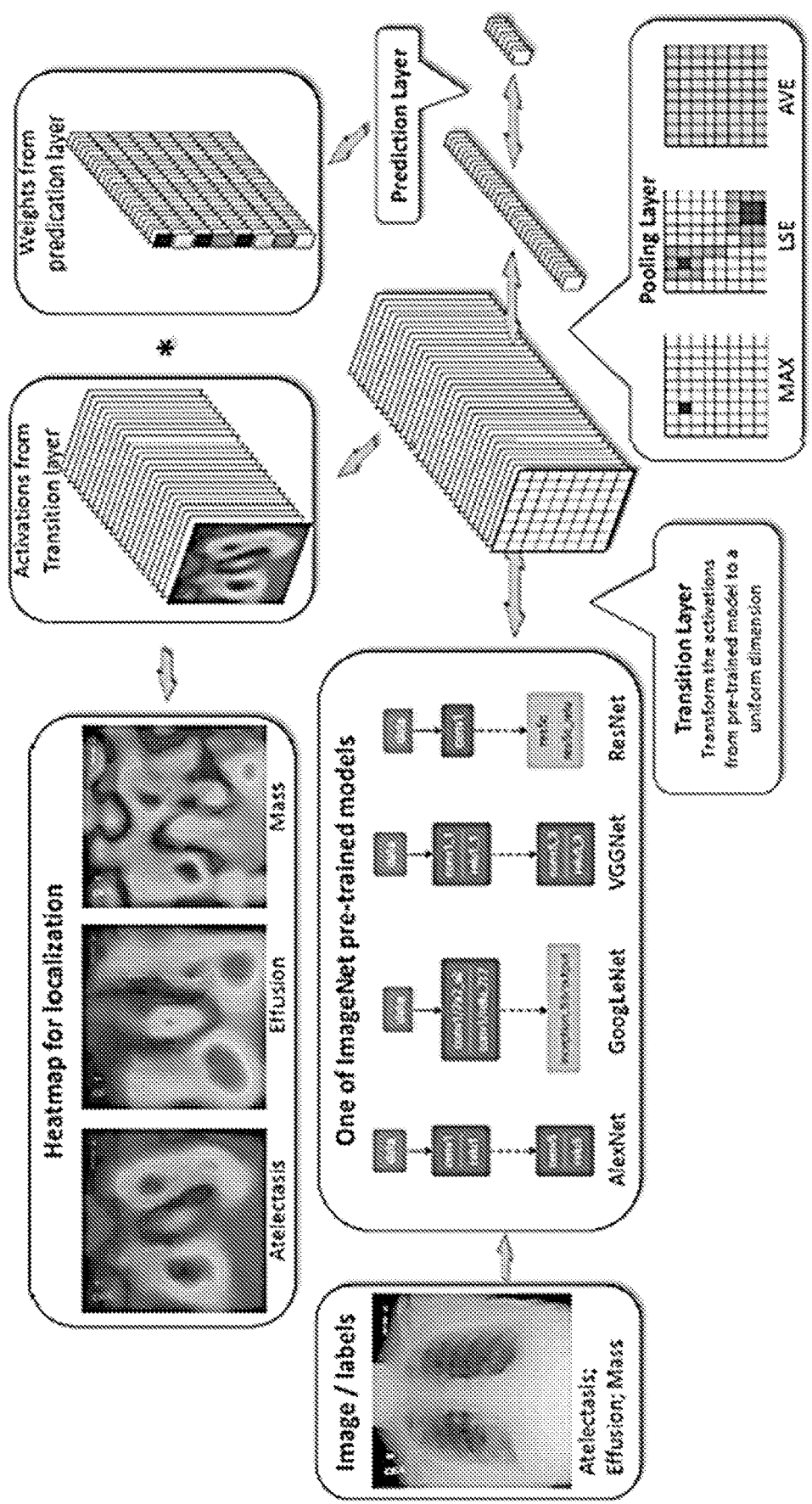
FIG. 4 is an overall flow-chart of a disclosed unified DCNN framework and disease localization process.

One goal is to first detect if one or multiple pathologies are presented in each X-ray image and later we can locate them using the activation and weights extracted from the network. We tackle this problem by training a multi-label DCNN classification model. FIG. 4 illustrates the DCNN architecture we adapted, with similarity to several previous weakly-supervised object localization methods. As shown in FIG. 4, we perform the network surgery on the pre-trained models (using ImageNet), e.g., AlexNet, GoogLeNet, VGG-Net-16, and ResNet-50, by leaving out the fully-connected layers and the final classification layers. Instead we insert a transition layer, a global pooling layer, a prediction layer and a loss layer in the end (after the last convolutional layer). A combination of deep activations from the transition layer (a set of spatial image features) and the weights of prediction inner-product layer (trained feature weighting) can enable us to find the plausible spatial locations of diseases.

Multi-label Setup: There are several options of image-label representation and the choices of multi-label classification loss functions. Here, we define a 8-dimensional label vector $y=[y_1, \ldots, y_c, \ldots, y_C], y_c \in \{0,1\}, C=8$ for each image. $y_c$ indicates the presence with respect to according pathology in the image while an all-zero vector $[0,0,0,0,0,0,0,0]$ represents the status of "Normal" (no pathology is found in the scope of any of 8 disease categories as listed). This definition transits the multi-label classification problem into a regression-like loss setting.

Transition Layer: Due to the large variety of pre-trained DCNN architectures we adopt, a transition layer is usually required to transform the activations from previous layers into a uniform dimension of output, $S \times S \times D, S \in \{8,16,32\}$. D represents the dimension of features at spatial location $(i,j), i,j \in \{1, \ldots, S\}$, which can be varied in different model settings, e.g., D=1024 for GoogLeNet and D=2048 for ResNet. The transition layer helps pass down the weights from pre-trained DCNN models in a standard form, which is critical for using this layers' activations to further generate the heatmap in pathology localization step.

Multi-label Classification Loss Layer: We first experiment 3 standard loss functions for the regression task instead of using the softmax loss for traditional multi-class classification model, i.e., Hinge Loss (HL), Euclidean Loss (EL) and Cross Entropy Loss (CEL). However, we find that the model has difficulty learning positive instances (images with pathologies) and the image labels are rather sparse, meaning there are extensively more '0's than '1's. This is due to our one-hot-like image labeling strategy and the unbalanced numbers of pathology and "Normal" classes. Therefore, we introduce the positive/negative balancing factor $\beta_P, \beta_N$ to enforce the learning of positive examples. For example, the weighted CEL (W-CEL) is defined as follows, $$L_{W\text{-}CEL}(f(\vec{x}), \vec{y}) = \beta_P \sum_{y_c=1} -\ln(f(x_c)) + \beta_N \sum_{y_c=0} -\ln(1-f(x_c)), \quad (1)$$

where $\beta_P$ is set to $$\frac{|P|+|N|}{|P|}$$

while $\beta_N$ is set to $$\frac{|P|+|N|}{|P|} \cdot |P|$$

and |N| are the total number of '1's and '0's in a batch of image labels.

Global Pooling Layer and Prediction Layer: In our multi-label image classification network, the global pooling and the predication layer are designed not only to be part of the DCNN for classification but also to generate the likelihood map of pathologies, namely a heatmap. The location with a peak in the heatmap generally corresponds to the presence of disease pattern with a high probability. The upper part of FIG. 4 demonstrates the process of producing this heatmap. By performing a global pooling after the transition layer, the weights learned in the prediction layer can function as the weights of spatial maps from the transition layer. Therefore, we can produce weighted spatial activation maps for each disease class (with a size of S×S×C) by multiplying the activation from transition layer (with a size of S×S×D) and the weights of prediction layer (with a size of D×C).

The pooling layer plays an important role that chooses what information to be passed down. Besides the conventional max pooling and average pooling, we also utilize the Log-Sum-Exp (LSE) pooling proposed in. The LSE pooled value $x_p$ is defined as $$x_p = \frac{1}{r} \cdot \log\left[\frac{1}{S} \cdot \sum_{(i,j)\in S} \exp(r \cdot x_{ij})\right], \quad (2)$$

where $x_{ij}$ is the activation value at (i,j), (i,j) is one location in the pooling region S, and S=s×s is the total number of locations in S. By controlling the hyper-parameter r, the pooled value ranges from the maximum in S (when r→∞) to average (r→0). It serves as an adjustable option between max pooling and average pooling. Since the LSE function suffers from overflow/underflow problems, the following equivalent is used while implementing the LSE pooling layer in our own DCNN architecture, $$x_p = x^* + \frac{1}{r} \cdot \log\left[\frac{1}{S} \cdot \sum_{(i,j)\in S} \exp(r \cdot (x_{ij} - x^*))\right], \quad (3)$$

where $x^* = \max\{|x_{ij}|, (i,j)\in S\}$.

Bounding Box Generation: The heatmap produced from our multi-label classification framework indicates the approximate spatial location of one particular thoracic disease class each time. Due to the simplicity of intensity distributions in these resulting heatmaps, applying an ad-hoc thresholding based B-Box generation method for this task is found to be sufficient. The intensities in heatmaps are first normalized to [0,255] and then thresholded by {60,180} individually. Finally, B-Boxes are generated to cover the isolated regions in the resulting binary maps.

Experiments

Data: We evaluate and validate the unified disease classification and localization framework using the proposed ChestX-ray8 database. In total, 108,948 frontal-view X-ray images are in the database, of which 24,636 images contain one or more pathologies. The remaining 84,312 images are normal cases. For the pathology classification and localization task, we randomly shuffled the entire dataset into three subgroups for CNN fine-tuning via Stochastic Gradient Descent (SGD): i.e. training (70%), validation (10%) and testing (20%). We only report the 8 thoracic disease recognition performance on the testing set in our experiments. Furthermore, for the 983 images with 1,600 annotated B-Boxes of pathologies, these boxes are only used as the ground truth to evaluate the disease localization accuracy in testing (not for training purpose).

CNN Setting: Our multi-label CNN architecture is implemented using Caffe framework. The ImageNet pre-trained models, i.e., AlexNet, GoogLeNet, VGGNet-16 and ResNet-50 are obtained from the Caffe model zoo. Our unified DCNN takes the weights from those models and only the transition layers and prediction layers are trained from scratch.

Due to the large image size and the limit of GPU memory, it is necessary to reduce the image batch_size to load the entire model and keep activations in GPU while we increase the iter_size to accumulate the gradients for more iterations. The combination of both may vary in different CNN models but we set batch_size×iter_size=80 as a constant. Furthermore, the total training iterations are customized for different CNN models to prevent over-fitting. More complex models like ResNet-50 actually take less iterations (e.g., 10,000 iterations) to reach the convergence. The DCNN models are trained using a Dev-Box linux server with 4 Titan X GPUs.

Figure 5:
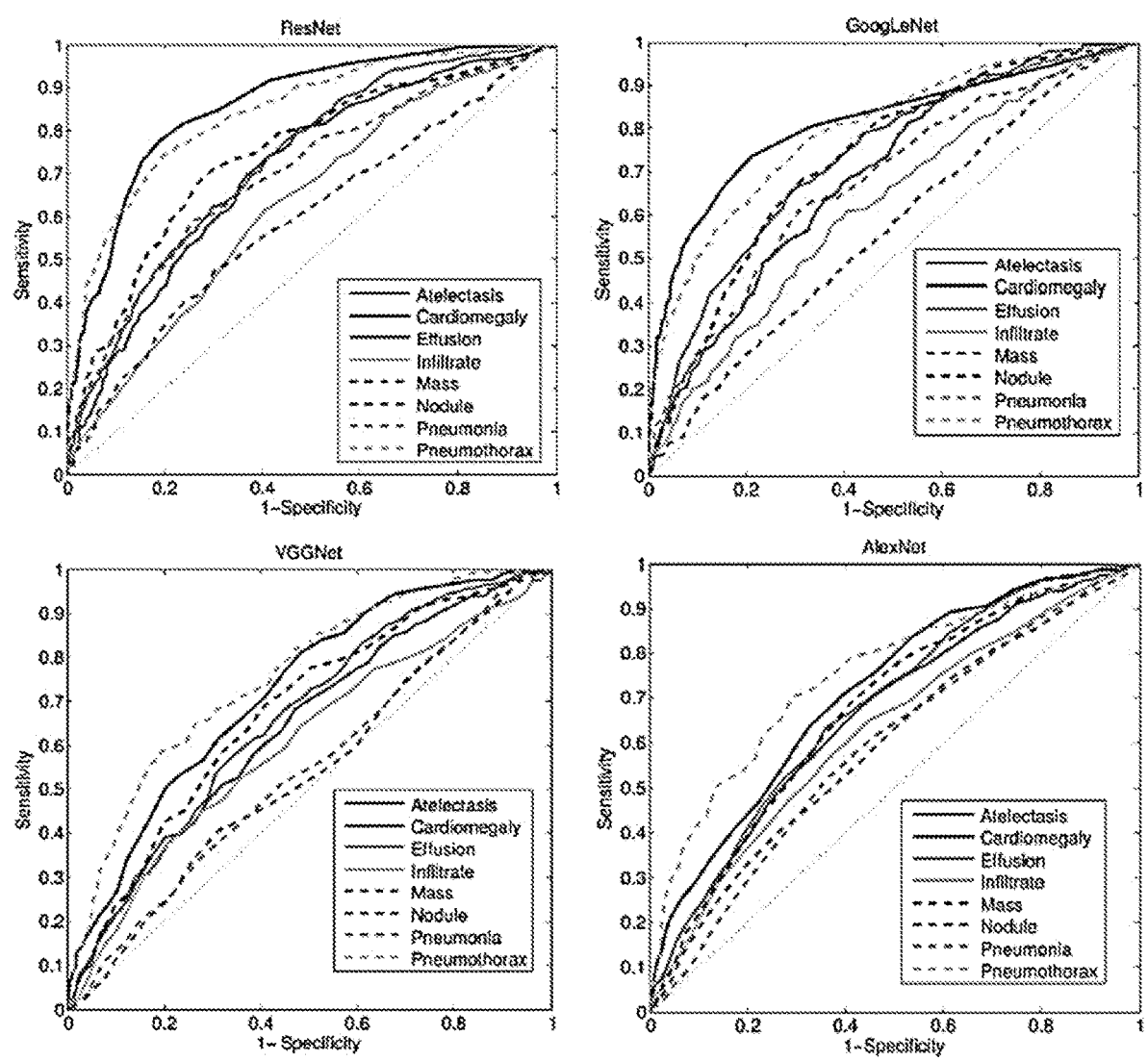
FIG. 5 is a comparison of multi-label classification performance with different model initializations.

Multi-label Disease Classification: FIG. 5 demonstrates the multi-label classification ROC curves on 8 pathology classes by initializing the DCNN framework with 4 different pre-trained models of AlexNet, GoogLeNet, VGG and ResNet-50. The corresponding Area-Under-Curve (AUC) values are given in Table 4. The quantitative performance varies greatly, in which the model based on ResNet-50 achieves the best results. The "Cardiomegaly" (AUC=0.8141) and "Pneumothorax" (AUC=0.7891) classes are consistently well-recognized compared to other groups while the detection ratios can be relatively lower for pathologies which contain small objects, e.g., "Mass" (AUC=0.5609) and "Nodule" classes. Mass is difficult to detect due to its huge within-class appearance variation. The lower performance on "Pneumonia" (AUC=0.6333) is probably because of lack of total instances in our patient population (less than 1% X-rays labeled as Pneumonia). This finding is consistent with the comparison on object detection performance, degrading from PASCAL VOC to MS COCO where many small annotated objects appear.

TABLE 3

AUCs of ROC curves for multi-label classification in different DCNN model setting.

| Setting | Atelectasis | Cardiomegaly | Effusion | Infiltration | Mass | Nodule | Pneumonia | Pneumothorax |
|---|---|---|---|---|---|---|---|---|
| Initialization with different pre-trained models | | | | | | | | |
| AlexNet | 0.6458 | 0.6925 | 0.6642 | 0.6041 | 0.5644 | 0.6487 | 0.5493 | 0.7425 |
| GoogleNet | 0.6307 | 0.7056 | 0.6876 | 0.6088 | 0.5363 | 0.5579 | 0.5990 | 0.7824 |
| VGGNet-16 | 0.6281 | 0.7084 | 0.6502 | 0.5896 | 0.5103 | 0.6556 | 0.5100 | 0.7516 |
| ResNet-50 | 0.7069 | 0.8141 | 0.7362 | 0.6128 | 0.5609 | 0.7164 | 0.6333 | 0.7891 |
| Different multi-label lass functions | | | | | | | | |
| CEL | 0.7064 | 0.7262 | 0.7351 | 0.6084 | 0.5530 | 0.6545 | 0.5164 | 0.7665 |
| W-CEL | 0.7069 | 0.8141 | 0.7362 | 0.6128 | 0.5609 | 0.7164 | 0.6333 | 0.7891 |

TABLE 4

Pathology localization accuracy and average false positive number for 8 disease classes.

| T(IoBB) | Atelectasis | Cardiomegaly | Effusion | Infiltration | Mass | Nodule | Pneumonia | Pneumothorax |
|---|---|---|---|---|---|---|---|---|
| T(IoBB) = 0.1 | | | | | | | | |
| Acc. | 0.7277 | 0.9931 | 0.7124 | 0.7886 | 0.4352 | 0.1645 | 0.7500 | 0.4591 |
| AFP | 0.0823 | 0.0487 | 0.0589 | 0.0426 | 0.0691 | 0.0630 | 0.0691 | 0.0264 |
| T(IoBB) = 0.25 (Two lines larger on both x and y axis than ground truth B-Boxes) | | | | | | | | |
| Acc. | 0.5500 | 0.9794 | 0.5424 | 0.5772 | 0.2823 | 0.0506 | 0.5583 | 0.3469 |
| AFP | 0.1666 | 0.1534 | 0.1189 | 0.0914 | 0.0975 | 0.0741 | 0.1250 | 0.0487 |
| T(IoBB) = 0.5 | | | | | | | | |
| Acc. | 0.2833 | 0.8767 | 0.3333 | 0.4227 | 0.1411 | 0.0126 | 0.3833 | 0.1836 |
| AFP | 0.2703 | 0.2611 | 0.1859 | 0.1422 | 0.1209 | 0.0772 | 0.1768 | 0.0772 |
| T(IoBB) = 0.75 | | | | | | | | |
| Acc. | 0.1666 | 0.7260 | 0.2418 | 0.3252 | 0.1176 | 0.0126 | 0.2583 | 0.1020 |
| AFP | 0.3048 | 0.3506 | 0.2113 | 0.1737 | 0.1310 | 0.0772 | 0.2184 | 0.0873 |
| T(IoBB) = 0.9 | | | | | | | | |
| Acc. | 0.1333 | 0.6849 | 0.2091 | 0.2520 | 0.0588 | 0.0126 | 0.2416 | 0.0816 |
| AFP | 0.3160 | 0.3983 | 0.2235 | 0.1910 | 0.1402 | 0.0772 | 0.2317 | 0.0904 |

Figure 6:
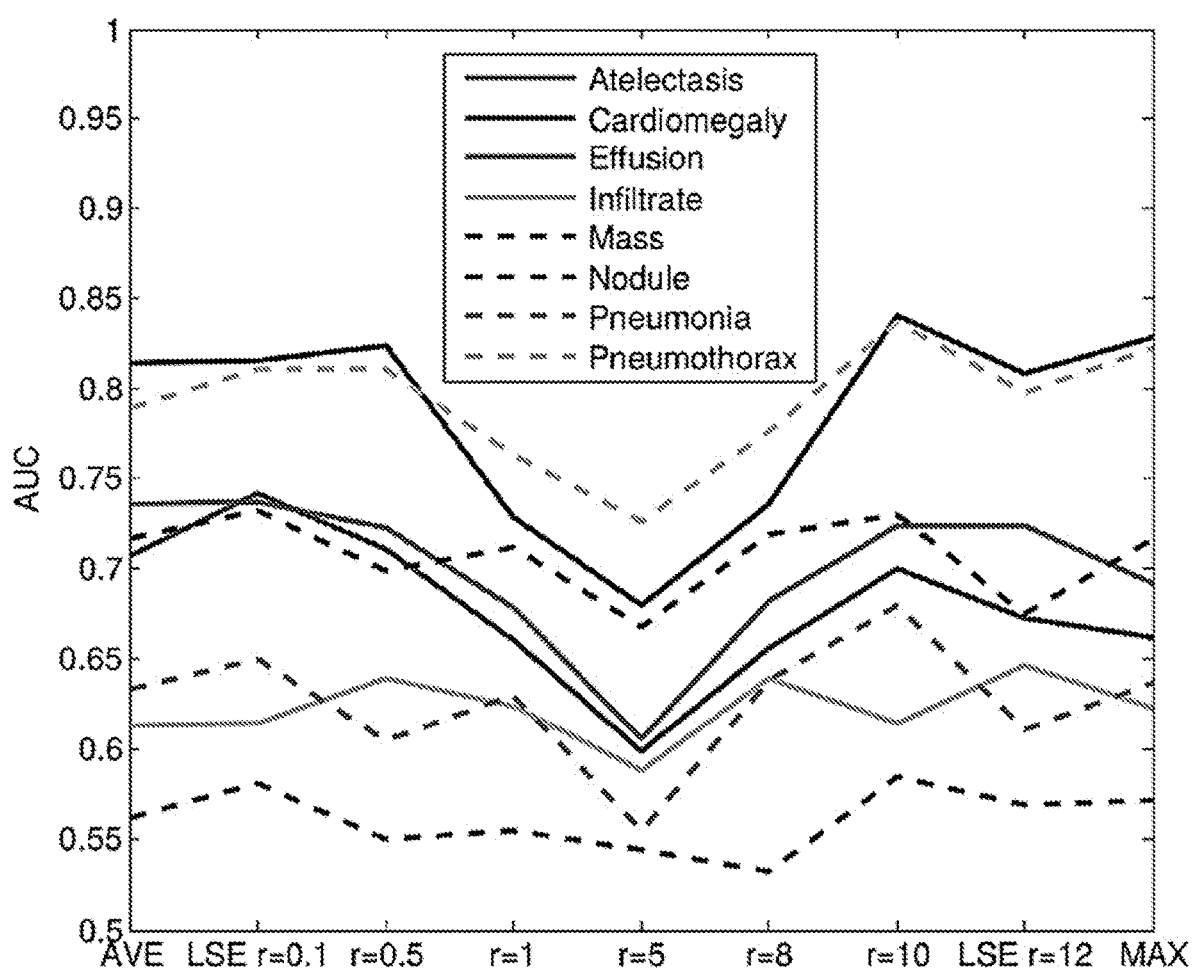
FIG. 6 is a comparison of a multi-label classification performance with different pooling strategies.
Figure 9:
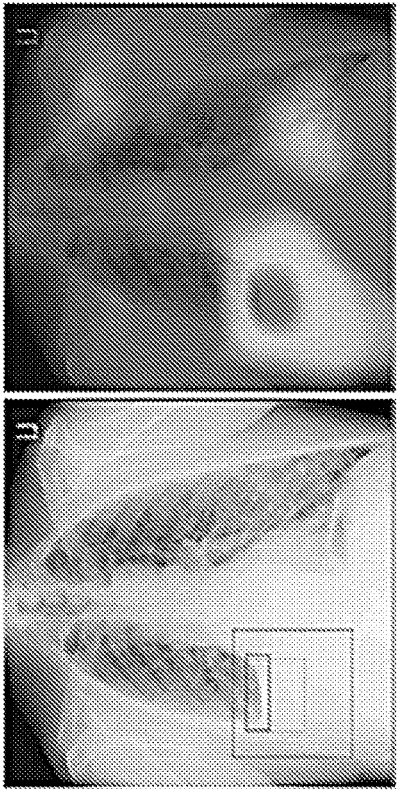
FIG. 9 is a sample of a chest x-ray radiology report, with mined disease keywords and localization result from the "Effusion" Class. Correct bounding box (in green), false positives (in red) and the ground truth (in blue) are plotted over the original image.
Figure 10:
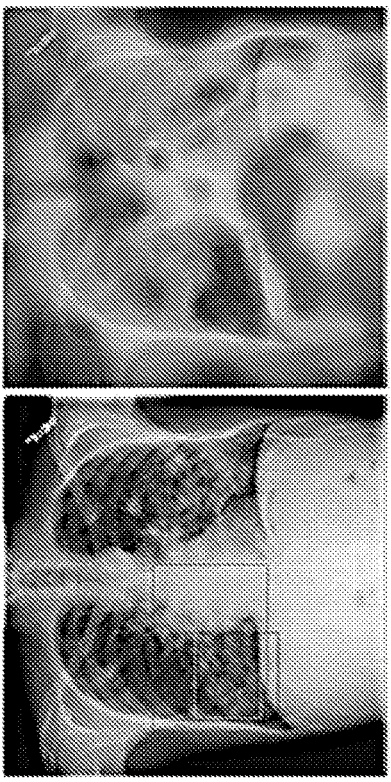
FIG. 10 is a sample of a chest x-ray radiology report, with mined disease keywords and localization result from the "Infiltration" Class. Correct bounding box (in green), false positives (in red) and the ground truth (in blue) are plotted over the original image.
Figure 11:
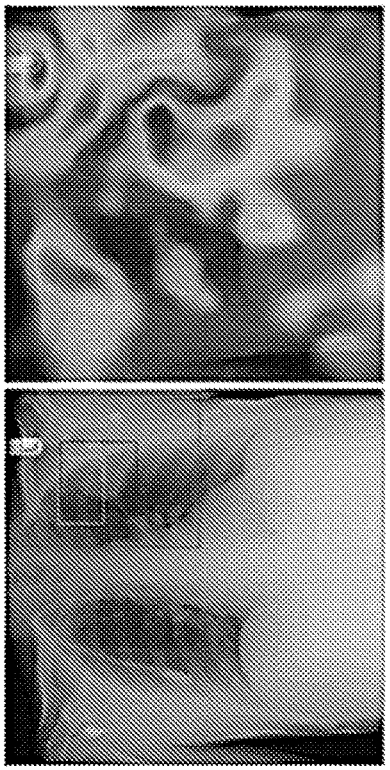
FIG. 11 is a sample of a chest x-ray radiology report, with mined disease keywords and localization result from the "Mass" Class. Correct bounding box (in green), false positives (in red) and the ground truth (in blue) are plotted over the original image.
Figure 12:
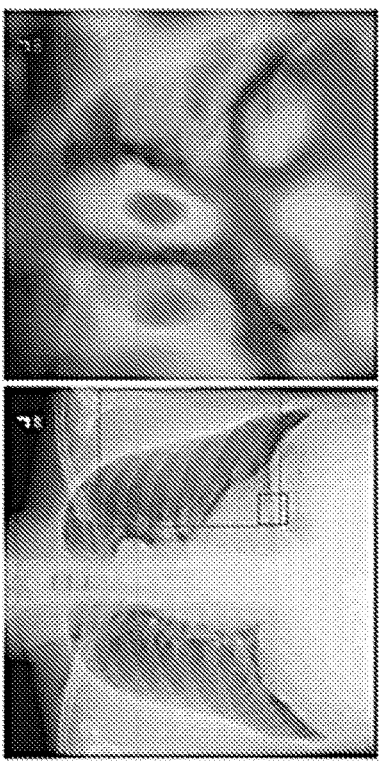
FIG. 12 is a sample of a chest x-ray radiology report, with mined disease keywords and localization result from the "Nodule" Class. Correct bounding box (in green), false positives (in red) and the ground truth (in blue) are plotted over the original image.
Figure 13:
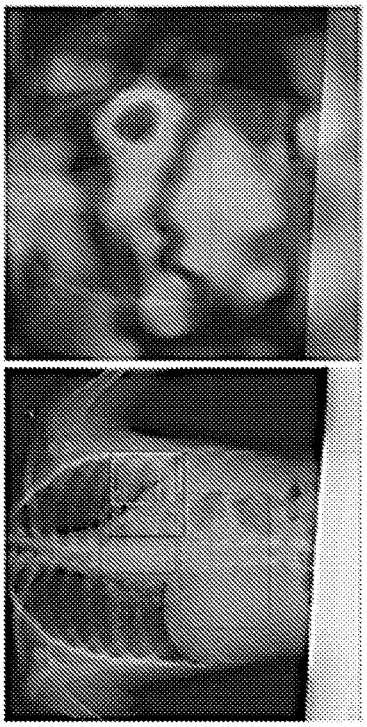
FIG. 13 is a sample of a chest x-ray radiology report, with mined disease keywords and localization result from the "Pneumonia" Class. Correct bounding box (in green), false positives (in red) and the ground truth (in blue) are plotted over the original image.
Figure 14:
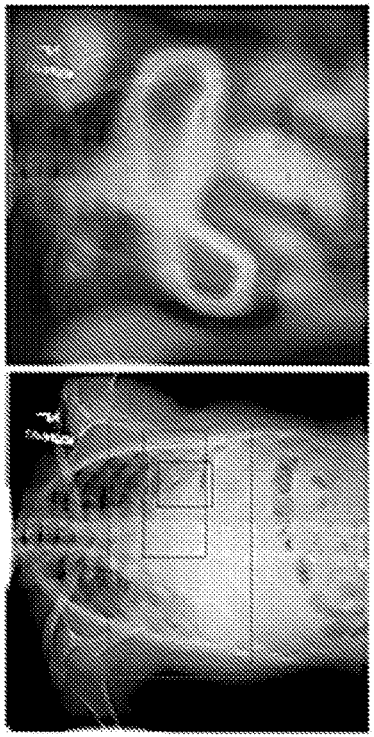
FIG. 14 is a sample of a chest x-ray radiology report, with mined disease keywords and localization result from the "Pneumothorax" Class. Correct bounding box (in green), false positives (in red) and the ground truth (in blue) are plotted over the original image.

Next, we examine the influence of different pooling strategies when using ResNet-50 to initialize the DCNN framework. As discussed above, three types of pooling schemes are experimented: average looping, LSE pooling and max pooling. The hyper-parameter r in LSE pooling varies in {0.1, 0.5, 1, 5, 8, 10, 12}. As illustrated in FIG. 6, average pooling and max pooling achieve approximately equivalent performance in this classification task. The performance of LSE pooling start declining first when r starts increasing and reach the bottom when r=5. Then it reaches the overall best performance around r=10. LSE pooling behaves like a weighed pooling method or a transition scheme between average and max pooling under different r values. Overall, LSE pooling (r=10) reports the best performance (consistently higher than mean and max pooling).

Last, we demonstrate the performance improvement by using the positive/negative instances balanced loss functions (Eq. 1). As shown in Table 4, the weighted loss (WCEL) provides better overall performance than CEL, especially for those classes with relative fewer positive instances, e.g. AUC for "Cardiomegaly" is increased from 0.7262 to 0.8141 and from 0.5164 to 0.6333 for "Pneumonia".

Disease Localization: Leveraging the fine-tuned DCNN models for multi-label disease classification, we can calculate the disease heatmaps using the activations of the transition layer and the weights from the prediction layer, and even generate the B-Boxes for each pathology candidate. The computed bounding boxes are evaluated against the hand annotated ground truth (GT) boxes (included in ChestX-ray8). Although the total number of B-Box annotations (1,600 instances) is relatively small compared to the entire dataset, it may be still sufficient to get a reasonable estimate on how the proposed framework performs on the weakly-supervised disease localization task. To examine the accuracy of computerized B-Boxes versus the GT B-Boxes, two types of measurement are used, i.e, the standard Intersection over Union ratio (IoU) or the Intersection over the detected B-Box area ratio (IoBB) (similar to Area of Precision or Purity). Due to the relatively low spatial resolution of heatmaps (32×32) in contrast to the original image dimensions (1024×1024), the computed B-Boxes are often larger than the according GT B-Boxes. Therefore, we define a correct localization by requiring either IoU>T(IoU) or IoBB>T(IoBB). Refer to the supplementary material for localization performance under varying T(IoU). Table 4 illustrates the localization accuracy (Acc.) and Average False Positive (AFP) number for each disease type, with T(IoBB) E {0.1, 0.25, 0.5, 0.75, 0.9}. See below for qualitative exemplary disease localization results for each of 8 pathology classes.

Constructing hospital-scale radiology image databases with computerized diagnostic performance benchmarks has not been addressed until this work. We attempt to build a "machine-human annotated" comprehensive chest X-ray database that presents the realistic clinical and methodological challenges of handling at least tens of thousands of patients (somewhat similar to "ImageNet" in natural images). We also conduct extensive quantitative performance benchmarking on eight common thoracic pathology classification and weakly-supervised localization using ChestX-ray8 database. Building large-scale, fully-automated high precision medical diagnosis systems can be performed using the disclosed technology. ChestX-ray8 can enable the data-hungry deep neural network paradigms to create clinically meaningful applications, including common disease pattern mining, disease correlation analysis, automated radiological report generation, etc. For future work, ChestX-ray8 will be extended to cover more disease classes and integrated with other clinical information, e.g., follow-up studies across time and patient history. The ChestX-ray8 dataset will be made publicly accessible upon institutional approval (in progress) and publication.

In some embodiments, only the semantic types of Diseases or Syndromes and Findings (namely 'dsyn' and 'fndg' respectively) are considered. Table 5 shows the corresponding SNOMED-CT concepts that are relevant to the target diseases (these mappings are developed by searching the disease names in the UMLS terminology service, and verified by a board certificated radiologist.

TABLE 5

Sample Targe Diseases and their corresponding concept and identifiers (CUIs) in SNOMED-CT.

| CUI | Concept |
|---|---|
| Atelectasis | |
| C0004144 | atelectasis |
| C0264494 | discoid atelectasis |
| C0264496 | focal atelectasis |
| Cardiomegaly | |
| C0018800 | cardiomegaly |
| Effusion | |
| C0013687 | effusion |
| C0031039 | pericardial effusion |
| C0032227 | pleural effusion disorder |
| C0747635 | bilateral pleural effusion |
| C0747639 | loculated pleural effusion |
| Pneumonia | |
| C0032285 | pneumonia |
| C0577702 | basal pneumonia |
| C0578576 | left upper zone pneumonia |
| C0578577 | right middle zone pneumonia |
| C0585104 | left lower zone pneumonia |
| C0585105 | right lower zone pneumonia |
| C0585106 | right upper zone pneumonia |
| C0747651 | recurent aspiration pneumonia |
| C1960024 | lingular pneumonia |
| Pneumothorax | |
| C0032326 | pneumothorax |
| C0264557 | chronic pneumothorax |
| C0546333 | right pneumothorax |
| C0546334 | left pneumothorax |

Although many text processing systems can handle the negation/uncertainty detection problem, most of them exploit regular expressions on the text directly. One of the disadvantages to use regular expressions for negation/uncertainty detection is that they cannot capture various syntactic constructions for multiple subjects. For example, in the phrase of "clear of A and B", the regular expression can capture "A" as a negation but not "B", particularly when both "A" and "B" are long and complex noun phrases.

To overcome this complication, we developed a number of novel rules of negation/uncertainty defined on the syntactic level. More specifically, we utilize the syntactic dependency information because it is close to the semantic relationship between words and thus has become prevalent in biomedical text processing. We defined our rules on the dependency graph, by utilizing the dependency label and direction information between words. Table 6 shows the rules we defined for negation/uncertainty detection on the syntactic level.

TABLE 6

Rules and corresponding examples for negation and uncertainty detection.

| Rule | Example |
|---|---|
| Negation | |
| no← * ← DISEASE | No acute pulmonary disease |
| * → prep_without → DISEASE | changes without focal airspace disease |
| clear/free/disappearance → prep_of → DISEASE | clear of focal airspace disease, pneumothorax, or pleural effusion |
| * → prep_without → evidence → prep_of → DISEASE | Changes without evidence of acute infiltrate |
| no ← neg ← evidence → prep_of → DISEASE | No evidence of active disease |
| Uncertainty | |
| cannot ← md ← exclude | The aorta is tortuous, and cannot exclude ascending aortic aneurysm |
| concern → prep_for → * | There is raises concern for pneumonia |
| could be/may be/... | which could be due to nodule/lymph node |
| difficult → prep_to → exclude | interstitial infiltrates difficult to exclude |
| may ← md ← represent | which may represent pleural reaction or small pulmonary nodules |
| suggesting/suspect/... → dobj → DISEASE | Bilateral pulmonary nodules suggesting pulmonary metastases |

Table 7 illustrates the localization accuracy (Acc.) and Average False Positive (AFP) number for each disease type, with IoU>T(IoU) only and T(IoU)∈{0.1, 0.2, 0.3, 0.4, 0.5, 0.6, 0.7}.

TABLE 7

Pathology localization accuracy and average false positive number for 8 disease classes with T(IoU) ranged from 0.1 to 0.7.

| T(IoU) | Atelectasis | Cardiomegaly | Effusion | Infiltration | Mass | Nodule | Pneumonia | Pneumothorax |
|---|---|---|---|---|---|---|---|---|
| T(IoU) = 0.1 | | | | | | | | |
| Acc. | 0.6888 | 0.9383 | 0.6601 | 0.7073 | 0.4000 | 0.1392 | 0.6333 | 0.3775 |
| AFP | 0.1443 | 0.2977 | 0.0934 | 0.1087 | 0.0934 | 0.0660 | 0.1839 | 0.0436 |
| T(IoU) = 0.2 | | | | | | | | |
| Acc. | 0.4722 | 0.6849 | 0.4509 | 0.4796 | 0.2588 | 0.0506 | 0.3500 | 0.2346 |
| AFP | 0.2327 | 0.4186 | 0.1686 | 0.1685 | 0.1209 | 0.0741 | 0.2428 | 0.0660 |
| T(IoU) = 0.3 | | | | | | | | |
| Acc. | 0.2444 | 0.4589 | 0.3006 | 0.2764 | 0.1529 | 0.0379 | 0.1666 | 0.1326 |
| AFP | 0.2916 | 0.4796 | 0.2063 | 0.2073 | 0.1341 | 0.0752 | 0.2703 | 0.0813 |
| T(IoU) = 0.4 | | | | | | | | |
| Acc. | 0.0944 | 0.2808 | 0.2026 | 0.1219 | 0.0705 | 0.0126 | 0.0750 | 0.0714 |
| AFP | 0.3282 | 0.5121 | 0.2296 | 0.2327 | 0.1432 | 0.0772 | 0.2876 | 0.0914 |
| T(IoU) = 0.5 | | | | | | | | |
| Acc. | 0.0500 | 0.1780 | 0.1111 | 0.0650 | 0.0117 | 0.0126 | 0.0333 | 0.0306 |
| AFP | 0.3384 | 0.5335 | 0.2510 | 0.2408 | 0.1483 | 0.0772 | 0.2926 | 0.0965 |
| T(IoU) = 0.6 | | | | | | | | |
| Acc. | 0.0222 | 0.0753 | 0.0457 | 0.0243 | 0.0000 | 0.0126 | 0.0166 | 0.0306 |
| AFP | 0.3434 | 0.5487 | 0.2642 | 0.2469 | 0.1493 | 0.0772 | 0.2957 | 0.0965 |
| T(IoU) = 0.7 | | | | | | | | |
| Acc. | 0.0055 | 0.0273 | 0.0196 | 0.0000 | 0.0000 | 0.0000 | 0.0083 | 0.0204 |
| AFP | 0.3465 | 0.5558 | 0.2682 | 0.2500 | 0.1493 | 0.0782 | 0.2967 | 0.0975 |

FIGS. 7-14 illustrate localization results from each of 8 disease classes together with associated report and mined disease keywords. The heatmaps overlay on the original images are shown on the right. Correct bounding boxes (in green), false positives (in red) and the groundtruth (in blue) are plotted over the original image on the left.

In order to quantitatively demonstrate how informative those heatmaps are, a simple two-level thresholding based bounding box generator is adopted here to catch the peaks in the heatmap and later generated bounding boxes can be evaluated against the ground truth. Each heatmap will approximately result in 1-3 bounding boxes. The localization accuracy and AFP (shown in Table 7) can be further optimized by adopting a more sophisticated bounding box generation method, e.g. selective search or Edgebox. With this technology, is can be possible to compute the exact spatial location of disease patterns, or to just obtain some instructive location information for future applications, e.g. automated radiological report generation. Take the case shown in FIG. 7 for an example. The peak at the lower part of the left lung region indicates the presence of "atelectasis", which confer the statement of " . . . stable abnormal study including left basilar infilrate/atelectasis, . . . " presented in the impression section of the associated radiological report. By combining with other information, e.g. a lung region mask, the heatmap itself is already more informative than just the presence indication of certain disease in an image.

As used herein, "image" refers to a visual image such as presented on a display device, or image data stored in one or more computer-readable media devices such as random access memory (RAM), hard disks, hard drives, CDs, DVDs. Such data can be stored in a variety of formats such as JEPG, TIFF, BMP, PNG, GIF, and others.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Characteristics and features described in conjunction with a particular aspect, embodiment, or example of the disclosed technology are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Figure 15:
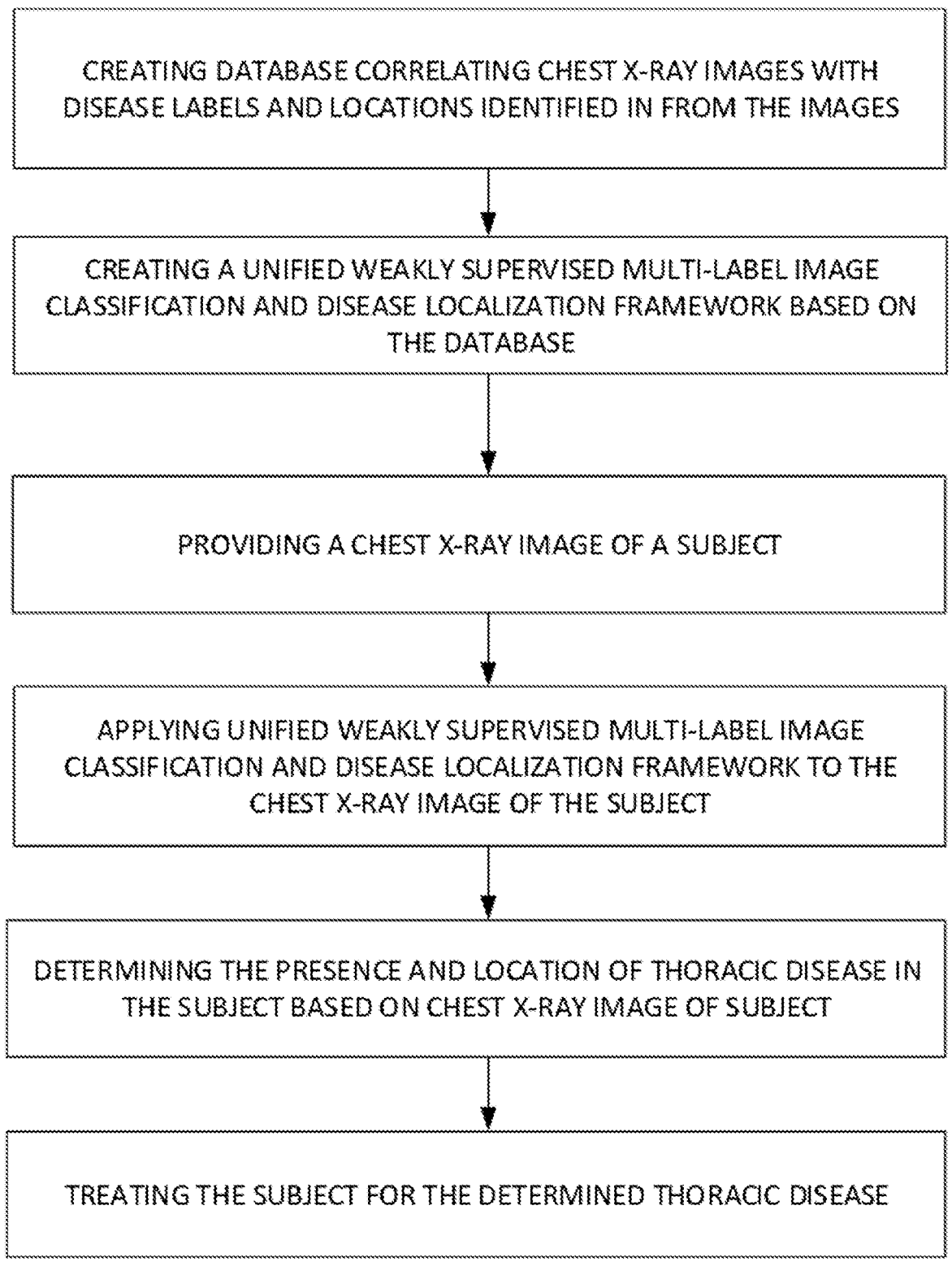
FIG. 15 is a flowchart illustrating exemplary method steps disclosed herein.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. For example, FIG. 15 is a flow diagram including several exemplary steps, yet any combination of these steps, in any logical order, can be performed to carry out many different methods, all of which methods are intended to be supported and encompassed by this disclosure. Various other steps or variations of the illustrated steps, can also be included in various methods as part of the disclosed technology. Moreover, for the sake of simplicity, the attached figures may not show the various ways in which the disclosed methods can be used in conjunction with other methods.

In some examples, values, procedures, or apparatus' are referred to as "lowest", "best", "minimum," or the like. It will be appreciated that such descriptions are intended to indicate that a selection among many used functional alternatives can be made, and such selections need not be better, smaller, or otherwise preferable to other selections.

As used herein, the terms "a", "an", and "at least one" encompass one or more of the specified element. That is, if two of a particular element are present, one of these elements is also present and thus "an" element is present. The terms "a plurality of" and "plural" mean two or more of the specified element. As used herein, the term "and/or" used between the last two of a list of elements means any one or more of the listed elements. For example, the phrase "A, B, and/or C" means "A", "B,", "C", "A and B", "A and C", "B and C", or "A, B, and C." As used herein, the term "coupled" generally means physically coupled or linked and does not exclude the presence of intermediate elements between the coupled items absent specific contrary language.

Figure 16:
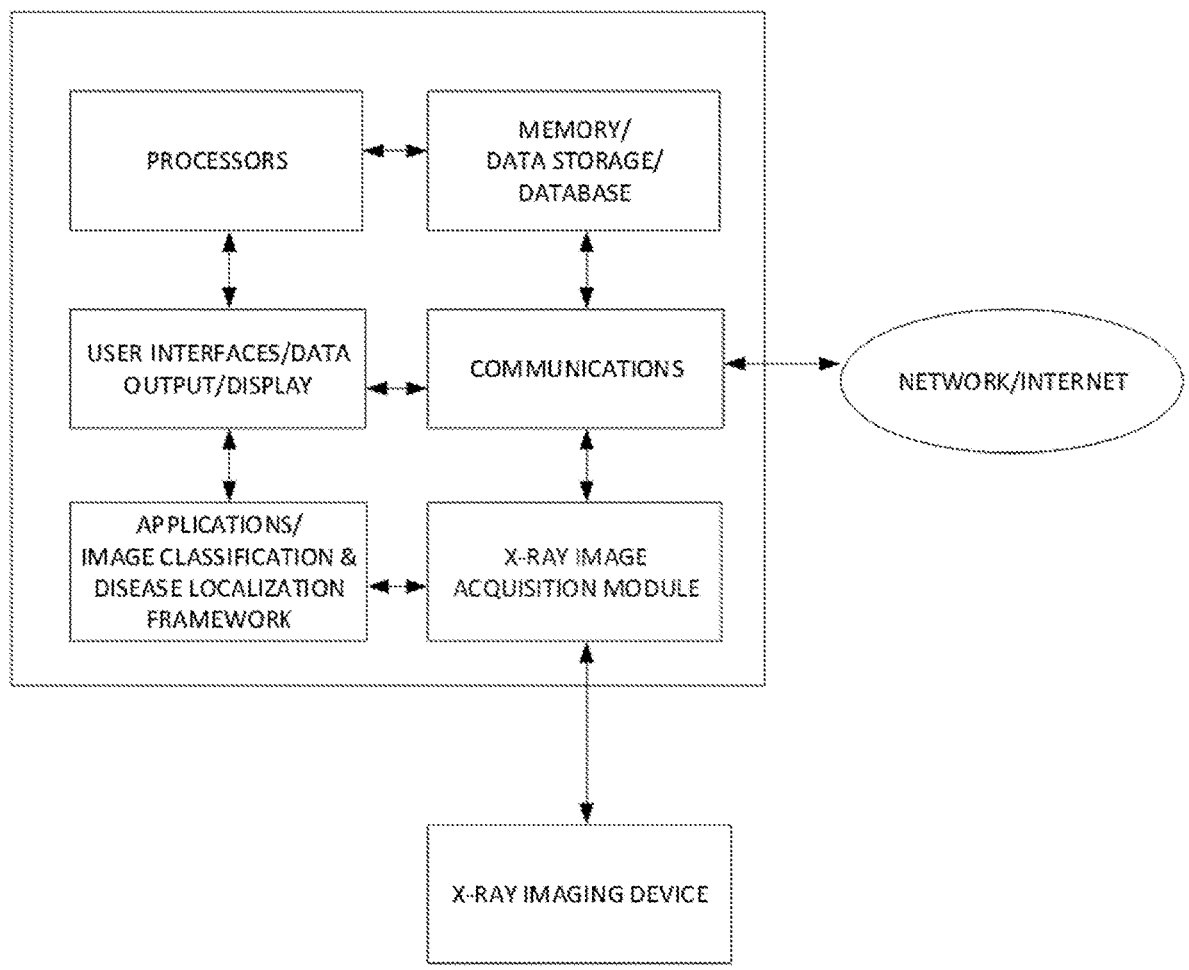
FIG. 16 is a schematic representation of an exemplary computing system disclosed herein.

The following discussion is intended to provide a brief description of an exemplary computing/data acquisition/application environment in which the disclosed technology may be implemented. FIG. 16 illustrates an exemplary system that includes a processor, memory/data storage/database, user interfaces, communications, x-ray image acquisition module, and applications configured to perform methods and operations disclosed herein. Although not required, the disclosed technology can be implemented at least in part in the general context of computer executable instructions, such as program modules, being executed by a personal computer (PC), a mobile computing device, tablet computer, or other computational and/or control device. Generally, program modules include routines, programs, objects, components, data structures, etc., that perform particular tasks or implement particular abstract data types. Moreover, the disclosed technology may be implemented with other computer system configurations, including hand held devices, multiprocessor systems, microprocessor-based or programmable consumer electronics, network PCs, minicomputers, mainframe computers, and the like. The disclosed technology may also be practiced in distributed computing environments where tasks are performed by remote processing devices that are linked through a communications network. In a distributed computing environment, program modules may be located in both local and remote memory storage devices.

An exemplary system for implementing the disclosed technology can include a general purpose computing device in the form of an exemplary PC, including one or more processing units, a system memory, and a system bus that couples various system components including the system memory to the one or more processing units. The system bus may be any of several types of bus structures including a memory bus or memory controller, a peripheral bus, and a local bus using any of a variety of bus architectures. The exemplary system memory includes read only memory (ROM) and random access memory (RAM). A basic input/output system (BIOS), containing the basic routines that help with the transfer of information between elements within the PC, is stored in ROM.

An exemplary PC can further include one or more storage devices such as a hard disk drive for reading from and writing to a hard disk, a magnetic disk drive for reading from or writing to a removable magnetic disk, an optical disk drive for reading from or writing to a removable optical disk (such as a CD-ROM or other optical media), and a solid state drive. Such storage devices can be connected to the system bus by a hard disk drive interface, a magnetic disk drive interface, an optical drive interface, or a solid state drive interface, respectively. The drives and their associated computer readable media provide nonvolatile storage of computer-readable instructions, data structures, program modules, and other data for the PC. Other types of computer-readable media which can store data that is accessible by a PC, such as magnetic cassettes, flash memory cards, digital video disks, CDs, DVDs, RAMs, ROMs, and the like, may also be used in the exemplary operating environment.

A number of program modules may be stored in the storage devices including an operating system, one or more application programs, other program modules, and program data. A user may enter commands and information into the PC through one or more input devices such as a keyboard and a pointing device such as a mouse. Other input devices may include a digital camera, microphone, joystick, game pad, scanner, or the like. These and other input devices are often connected to the one or more processing units through a serial port interface that is coupled to the system bus, but may be connected by other interfaces such as a parallel port, game port, or universal serial bus (USB). A monitor or other type of display device is also connected to the system bus via an interface, such as a video adapter. Other peripheral output devices, such as speakers and printers (not shown), may be included.

The PC may operate in a networked environment using logical connections to one or more remote computers. In some examples, one or more network or communication connections are included. A remote computer may be another PC, a server, a router, a network PC, or a peer device or other common network node, and typically includes many or all of the elements described above relative to the PC. The local computer and/or the remote computer can be connected to a logical a local area network (LAN) and a wide area network (WAN). Such networking environments may include wide computer networks, intranets, and the Internet.

When used in a LAN networking environment, the PC is connected to the LAN through a network interface. When used in a WAN networking environment, the PC typically includes a modem or other means for establishing communications over the WAN, such as the Internet. In a networked environment, program modules depicted relative to the personal computer, or portions thereof, may be stored in the remote memory storage device or other locations on the LAN or WAN. The network connections shown are exemplary, and other means of establishing a communications link between the computers may be used.

The memory generally includes computer-executable instructions for performing aspects of the disclosed methods in respective memory portions. Computer-executable instructions for data acquisition and/or other aspects of the disclosed methods can be stored in a specific memory portion for use with an X-ray machine or other equipment. Acquired and processed data can be displayed using computer-executable instructions stored at the memory portion. As noted above, data acquisition, processing, and instrument control can be provided at any portion of the system, or distribution at one or more processing devices using a LAN or WAN.

In view of the many possible embodiments to which the principles of the disclosed technology may be applied, it should be recognized that the illustrated embodiments are only examples and should not be taken as limiting the scope of the disclosure. Rather, the scope of the disclosure is at least as broad as the following claims. We therefore claim all that comes within the scope of the following claims.

What is claimed is:

1. A method comprising:
providing a chest x-ray image of a subject; and
by a computing system, analyzing the chest x-ray image of the subject by applying a unified weakly supervised multi-label image classification and disease localization framework to the chest x-ray image of the subject and determining a presence and anatomical locations of one or more thoracic diseases in the subject based on the analysis of the chest x-ray image wherein the unified weakly supervised multi-label image classification and disease localization framework comprises a multi-label DCNN classification model, wherein the DCNN comprises a transition layer, a global pooling layer, a prediction layer, and a multi-label classification loss layer in an end after a last convolutional layer.

2. The method of claim 1, wherein the anatomical locations of the one or more thoracic diseases are identified with one or more bounding boxes localized relative to the chest x-ray images.

3. The method of claim 2, further comprising generating an automated radiological report corresponding to the x-ray image of the subject based on the determined presence and anatomical locations of the one or more thoracic diseases in the subject.

4. The method of claim 2, wherein the determining utilizes a database containing a plurality of chest x-ray images and a plurality of corresponding thoracic diseases and locations associated with the plurality of chest x-ray images, the plurality of corresponding thoracic diseases and locations having been text-mined from radiological reports corresponding to the plurality of chest x-ray images using natural language processing.

5. The method of claim 2, wherein the one or more thoracic diseases comprise Atelectasis, Cardiomegaly, Effusion, Infiltration, Mass, Nodule, Pneumonia, and Pneumathorax.

6. The method of claim 1, wherein Deep Convolutional Neural Network (DCNN) architectures are used for the weakly-supervised disease localization.

7. The method of claim 1, wherein spatial locations of diseases are determined using a combination of deep activations from the transition layer and weights of the prediction layer.

8. The method of claim 1, wherein the transition layer transforms the activations from previous layers into a uniform dimension of output.

9. A computer readable storage device comprising computer-executable instructions for performing the method of claim 1.

10. The method of claim 1, further comprising treating the subject for the determined thoracic diseases.

11. A system comprising:
a computer processor; and
a data storage device that stores a database comprising:
a plurality of chest x-ray images; and
disease labels and locations associated with each chest x-ray image;
wherein the disease labels and locations are mined from radiological reports associated with the chest x-ray images, the disease labels identifying thoracic diseases indicated by the corresponding chest x-ray images, and the locations identifying anatomical areas in the chest x-ray images where the indicated thoracic diseases are located;
wherein the computer processor is operable to receive or generate a chest x-ray image of a subject and to determine presence and anatomical locations of one or more thoracic diseases in the subject based on automated analysis of the chest x-ray image of the subject using a unified weakly supervised multi-label image classification and disease localization framework wherein the unified weakly supervised multi-label image classification and disease localization framework comprises a multi-label DCNN classification model, wherein the DCNN comprises a transition layer, a global pooling layer, a prediction layer and a multi-label classification loss layer.

12. The system of claim 11, wherein the system is further operable to generate a radiological report corresponding to the x-ray image of the subject based on the determined presence and anatomical locations of the one or more thoracic diseases in the subject.

13. The system of claim 11, wherein the thoracic diseases comprise Atelectasis, Cardiomegaly, Effusion, Infiltration, Mass, Nodule, Pneumonia, and Pneumathorax.

14. The system of claim 11, wherein the anatomical locations of the one or more thoracic diseases are identified with one or more bounding boxes localized relative to the chest x-ray images.

15. The system of claim 11, wherein the system uses Deep Convolutional Neural Network (DCNN) architectures for weakly-supervised object localization.

16. The system of claim 11, wherein spatial locations of diseases are determined using a combination of deep activations from the transition layer and weights of the prediction layer.

17. The system of claim 11, further comprising an x-ray imaging device that generates the chest x-ray of the subject.

18. A computer readable storage device comprising the database of claim 11.

* * * * *